United States Patent [19]

Dong et al.

[11] 4,190,661
[45] Feb. 26, 1980

[54] PYRAZOLO-QUINOLINES, COMPOSITIONS AND PHARMACEUTICAL PREPARATIONS

[75] Inventors: P. Le Hao Dong, Montpellier; Claude Coquelet, St. Gely du Fesc, both of France

[73] Assignee: Laboratoires Chauvin-Blache, Montpellier, France

[21] Appl. No.: 906,410

[22] Filed: May 16, 1978

[30] Foreign Application Priority Data

May 20, 1977 [FR] France .................................. 77 15573

[51] Int. Cl.$^2$ ...................... A61K 31/47; C07D 471/04
[52] U.S. Cl. ..................................... 424/258; 548/371;
424/250; 544/250; 546/82
[58] Field of Search .......................... 424/258; 546/82; 544/250

[56] References Cited

U.S. PATENT DOCUMENTS

| | | | |
|---|---|---|---|
| 3,506,667 | 4/1970 | Kaminsky | 546/83 |
| 3,714,170 | 1/1973 | Dohmori et al. | 546/83 |
| 3,868,378 | 2/1975 | Spencer et al. | 546/82 |
| 3,890,324 | 6/1975 | Katner | 546/82 |
| 4,109,091 | 8/1978 | Denzel et al. | 544/250 |

OTHER PUBLICATIONS

Koren et al., Tetrahydron, (1975) pp. 493–497.
Morrison et al., Organic Chemistry, (1966) p. 1075.

*Primary Examiner*—David Wheeler
*Attorney, Agent, or Firm*—Young & Thompson

[57] ABSTRACT

This invention relates to compounds having the formula:

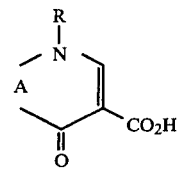

in which: R represents a $C_{1-6}$ alkyl radical or a $C_{1-6}$ alkenyl radical; A represents an indazol-2,3- or 4,5- or 6,7-diyl radical, which indazoldiyl radical may be substituted on the nitrogen atoms at 1- or 2-position with $C_{1-6}$ alkyl or phenyl-($C_{1-6}$) alkyl radicals, and their salts with pharmaceutically acceptable bases.

Said compounds are therapeutically useful as antibacterial agents.

6 Claims, No Drawings

PYRAZOLO-QUINOLINES, COMPOSITIONS AND PHARMACEUTICAL PREPARATIONS

This invention relates to new indazole derivatives, to a process for their preparation and to their therapeutic applications.

This invention relates to compounds having the formula:

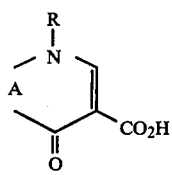

in which:

R represents a $C_{1-6}$ alkyl radical or a $C_{1-6}$ alkenyl radical, particularly ethyl or vinyl, A represents an indazol-2,3- or -4,5- or 6,7-diyl radical, which indazoldiyl radical may be substituted on the nitrogen atoms at 1- or 2-position with $C_{1-6}$ alkyl or phenyl-($C_{1-6}$)alkyl radicals, particularly with methyl, ethyl and benzyl radicals, and their salts with pharmaceutically acceptable bases.

The compounds of the formula (I) may be prepared according to the following reaction scheme:

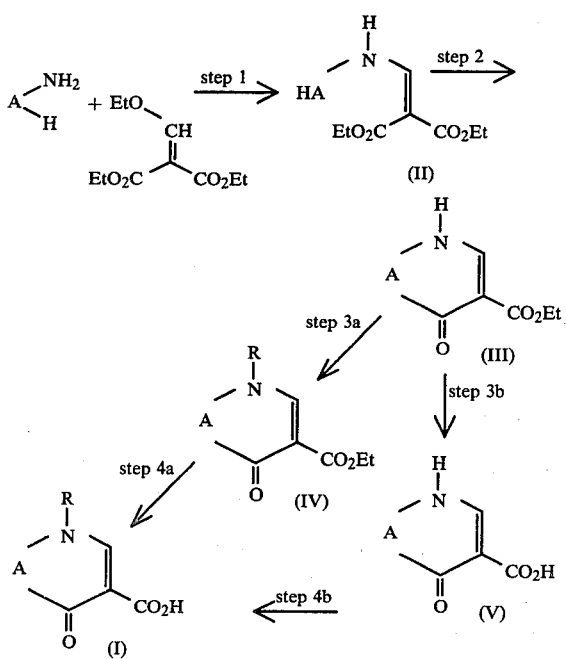

In a first step, an amine having the formula $AHNH_2$ is condensed with ethyl ethoxymethylene malonate to give a compound of the formula (II). Said condensation is effected by heating in the absence of solvent, or within an inert solvent heat transfer medium, the reaction temperature being about 100° C. Toluene is typically used as solvent.

In a second step, the compound of the formula (II) is cyclized to a compound of the formula (III) by heating at elevated temperature within a suitable solvent used as heat transfer medium. Gilotherm and Dowtherm are solvents useful for this type of reaction which requires a temperature of about 250° C. (step 2).

Alkylation or alkenylation of the esters of the formula (III) according to conventional methods leads to N-substituted compounds of the formula (IV) (step 3a).

Hydrolysis of the latter compounds gives compounds of the formula (I) (step 4a).

The derivatives of the general formula (I) may also be obtained by hydrolysis of esters of the formula (III) to compounds of the formula (V) (step 3b) and subsequent alkylation or alkenylation of the compounds of the formula (V) (step 4b).

The preparation of compounds of the formula (I) is illustrated in the following non-limiting Examples.

A—Preparation of compounds of the general formula (II)

EXAMPLE 1

Ethyl indazol-4-yl-aminomethylene malonate (IIb)

A mixture of 4-amino-indazole (0.05 mole) and ethyl ethoxymethylene malonate (0.055 mole) is maintained for 30 minutes at 110° C., with mechanical stirring. After cooling, the resulting ethyl indazolylaminomethylene-malonate crystals are suction filtered, washed with ether-petroleum ether and dried in vacuo at room temperature.

The product is obtained as yellow crystals, M.p.=168°–70° C. (Koeffler block).

The characteristics of the compound thus prepared are tabulated in following Table I, together with those of other compounds of the formula (II) prepared in an analogous manner.

For any run involving larger amounts of materials, use of a solvent such as toluene, which promotes heat transfer, is required.

TABLE I

| | N° | Empirical formula | M.P.(°C.) and crystallization solvent | Yield % |
|---|---|---|---|---|
| 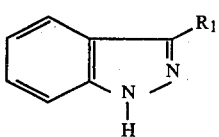 | IIa | $C_{15}H_{17}O_4N_3$ | 156–157 (benzene) | 70 |

TABLE I-continued

| N° | | Empirical formula | M.P.(°C.) and crystallization solvent | Yield % |
|---|---|---|---|---|
| IIb | (4-R₁-indazole, NH) | C₁₅H₁₇O₄N₃ | 168–170 (toluene) | 95 |
| IIc | (5-R₁-indazole, NH) | C₁₅H₁₇O₄N₃ | 163–165 (ethanol) | 90 |
| IId | (5-R₁-indazole, N-CH₂-φ) | C₂₂H₂₃O₄N₃ | 70–75 (ether) | 95 |
| IIe | (6-R₁-indazole, NH) | C₁₅H₁₇O₄N₃ | 164–165 (ethanol) | 75 |
| IIf | (6-R₁-indazole, N-CH₃) | C₁₆H₁₉O₄N₃ | 77–78 (ligroin) | 73 |
| IIg | (6-R₁-isoindazole, N-CH₃) | C₁₆H₁₉O₄N₃ | 112 (ligroin) | 98 |
| IIh | (7-R₁-indazole, NH) | C₁₅H₁₇O₄N₃ | 139–140 (ethanol) | 55 |

Note:
R₁ represents the radical —NH—CH=C(CO₂Et)₂

B—Preparation of compounds of the general formula (III)

EXAMPLE 2

3-Carbethoxy-4-oxo-pyrazolo[5,4-h]quinoline (IIIb)

Ethyl indazolylaminomethylene-malonate (IIb; 0.05 mole) is added portionwise to Gilotherm (200 ml) preheated to the boiling temperature (about 255° C.). After completion of the addition, the reaction mixture is maintained at 255° C. for 10 minutes. After cooling, the resulting 3-carbethoxy-4-oxo-pyrazolo[5,4-h]quinoline is suction filtered, the crystals are washed with alcohol to remove the Gilotherm and are then dried in vacuo.

The product is obtained as pale yellow crystals recrystallizable from dimethylformamide. M.p.=270° C.

The characteristics of the compound thus prepared are tabulated in following Table II, together with those of other compounds of the formula (III) prepared in an analogous manner.

TABLE II

| n° | | Empirical formula | M.P.(°C.) and crystallization solvent | Yield % |
|---|---|---|---|---|
| IIIa | (pyrazolo-quinoline with CO₂Et, =O) | C₁₃H₁₁O₃H₃ | 350 (DMF) | 90 |

TABLE II-continued
| | n° | Empirical formula | M.P.(°C.) and crystallization solvent | Yield % |
|---|---|---|---|---|
| 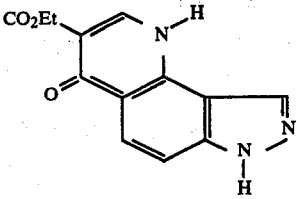 | IIIb | C₁₃H₁₁O₃H₃ | >270 (DMF) | 80 |
| 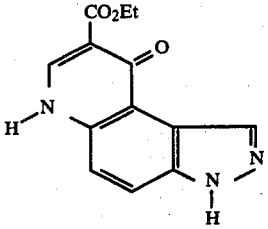 | IIIc | C₁₃H₁₁O₃N₃ | 336 (DMF) | 70 |
| 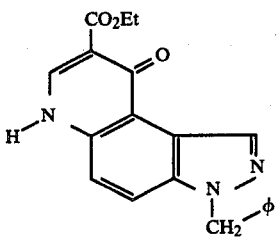 | IIId | C₂₀H₁₇O₃N₃ | >270 (DMF) | 40 |
| 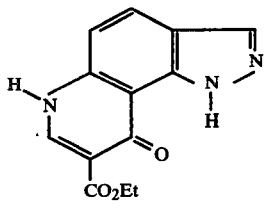 | IIIe | C₁₃H₁₁O₃N₃ | 328–329 (DMF) | 90 |
| 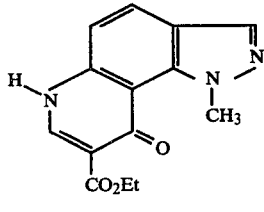 | IIIf | C₁₄H₁₃O₃N₃ | 304–305 (DMF) | 70 |
| 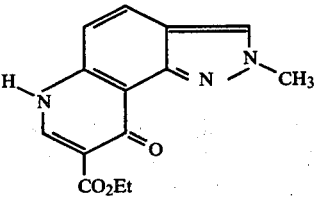 | IIIg | C₁₄H₁₃O₃N₃ | 278 (DMF) | 98 |
| 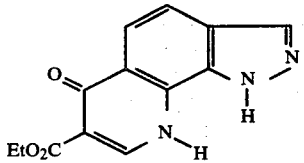 | IIIh | C₁₃H₁₁O₃N₃ | 303–304 (DMF) | 85 |

C—Preparation of compounds of the general formula (IV)

EXAMPLE 3

3-Oxo-4-carbethoxy-6-ethyl-pyrimido[3,2-h]indazole (IVa)

3-Oxo-4-carbethoxy-pyrimido[3,2-b]indazole (IIIa) (0.1 mole) and potassium carbonate (0.2 mole) in dimethylformamide (300 ml) are heated to 70° C. After complete dissolution of the ester, methyl iodide (25 ml) is added and heating is continued for 6 hours. After cooling, the insoluble fraction which contains the inorganic salts is suction filtered and the filtrate is evaporated in vacuo. The 3-oxo-4-carbethoxy-6-ethyl-pyrimido[3,2-b]crystals are suction filtered, washed with water and are then dried in vacuo.

After recrystallization from benzene, the product is obtained as light yellow crystals, M.p.=153°-154° C. (Koeffler block).

The characteristics of the product thus prepared are tabulated in Table III below, together with those of other compounds of the formula (IV) prepared in an analogous manner.

because hydrolysis is generally effected in situ, to give acids of the general formula (I).

D—Preparation of compounds of the general formula (V)

EXAMPLE 4

3-Carboxy-4-oxo-pyrazolo[5,4-h]quinoline (Vb)

3-Carbethoxy-4-oxo-pyrazolo[5,4-h]quinoline (0.05 mole) is added to a 10% sodium hydroxide solution (200 ml). The reaction mixture is refluxed for 3 hours, which time is required for complete dissolution to occur. The cold solution is made acidic with a dilute hydrochloric acid solution. The resulting 3-carboxy-4-oxo-pyrazolo[5,4-h]quinoline precipitates out. It is suction filtered, washed with water and dried in vacuo.

The crude product is recrystallized from dimethylformamide. M.p.=>270° C.

Hydrolysis is effected in an identical manner for the preparation of compounds of the formula (V) via hydrolysis of esters (III) and for the preparation of compounds of the formula (I) from compounds of the formula (IV).

The characteristics of the compounds prepared in

TABLE III

| | n° | Empirical formula | M.p. (°C.) and crystallization solvent | Yield % |
|---|---|---|---|---|
| (structure) | IVa | $C_{15}H_{15}O_3N_3$ | 152 (benzene) | 70 |
| (structure) | IVe | $C_{15}H_{15}O_3N_3$ | 240–241 (ethanol) | 85 |
| (structure) | IVh | $C_{15}H_{15}O_3N_3$ | 162–163 (ethanol) | 10 |

The other compounds of the formula (IV) obtained from compounds of the formula (III) were not isolated because hydrolysis is generally effected in situ, to give acids of the general formula (I).

Example 4 are tabulated in following Table IV, together with those of other compounds of the formula (V) prepared in an analogous manner.

TABLE IV

| | N° | Name | Empirical formula | M.p. (°C.) and crystallization solvent | Yield % |
|---|---|---|---|---|---|
|  | Vb | 3-carboxy-4-oxo-pyrazolo[5,4-h]quinoline | $C_{11}H_7O_3N_3$ | 270 (DMF) | 50 |

TABLE IV-continued

| N° | Name | Empirical formula | M.p. (°C.) and crystallization solvent | Yield % |
|---|---|---|---|---|
| Vc | 3-carboxy-4-oxo-pyrazolo[4,5-f]quinoline | $C_{11}H_7O_3N_3$ | 361 (DMF) | 70 |
| Vd | 3-carboxy-4-oxo-7-benzyl-pyrazolo[4,5-f]quinoline | $C_{18}H_{13}O_3N_3$ | 270 (DMF) | 90 |
| Ve | 3-carboxy-4-oxo-pyrazolo[5,4-f]quinoline | $C_{11}H_7O_3N_3$ | 338–39 (DMF) | 52 |
| Vf | 3-carboxy-4-oxo-5-methyl-pyrazolo[5,4-f]quinoline | $C_{12}H_9O_3N_3$ | 338–340 (DMF) | 95 |
| Vg | 3-carboxy-4-oxo-6-methyl-pyrazolo[3,4-f]quinoline | $C_{12}H_9O_3N_3$ | 360 (DMSO) | 95 |
| Vh | 3-carboxy-4-oxo-pyrazolo[4,5-h]quinoline | $C_{11}H_7O_3N_3$ | 315–316 (DMSO + $H_2O$) | 70 |

E—Preparation of compounds of the general formula (I)

EXAMPLE 5

1-Ethyl-3-carboxy-4-oxo-pyrazolo[4,5-f]quinoline (Ic)

A mixture of 3-carboxy-4-oxo-pyrazolo[4,5-f]quinoline (0.02 mole) and potassium carbonate (0.05 mole) in dimethylformamide (100 ml) is heated at 70° C. After dissolution of the acid, ethyl iodide (10 ml) is added and heating is continued for a further 12 hours. The inorganic salts are filtered off and the filtrate is evaporated off. The residue is dissolved hot in a 10% potassium hydroxide solution. After filtration, the filtrate is made acidic with a dilute hydrochloric acid solution.

1-Ethyl-3-carboxy-4-oxo-pyrazolo[4,5-f]quinoline (Ic) precipitates out as white crystals which are suction filtered, washed with water and dried in vacuo.

The crude product is recrystallized from dimethylformamide. M.p.=360° C.

EXAMPLE 6

1-Vinyl-3-carboxy-4-oxo-pyrazolo[5,4-f]quinoline (Ie′)

3-Carbethoxy-4-oxo-pyrazolo[5,4-f]quinoline (0.02 mole) and potassium carbonate (0.1 mole) in dimethylformamide (100 ml) are heated at 80° C. After complete dissolution of the ester, dibromoethane (0.1 mole) is added and heating is maintained for 12 hours. The insoluble material is filtered off and the filtrate is evaporated in vacuo. The residue is extracted with chloroform; the chloroform solution is evaporated after washing with water. The residue is refluxed for 2 hours in a 10% potassium hydroxide solution (100 ml). The cold solution is made acidic with dilute hydrochloric acid.

The 1-vinyl-3-carboxy-4-oxo-pyrazolo[5,4-f]quinoline crystals are suction filtered, washed with water and dried.

The crude material is recrystallized from dimethylformamide. M.p. = >270° C.

The characteristics of the compounds prepared in Examples 5 and 6 are tabulated in following Table V, together with those of other compounds of the formula (I) prepared in an analogous manner.

TABLE V

| N° | Name | Empirical Formula | M.p. (°C.) and crystallization solvent | Yield % |
|---|---|---|---|---|
| Ia | 3-oxo-4-carboxy-6-ethyl-pyrimido[3,2-b]indazole | $C_{13}H_{11}O_3N_3$ | 208–210 (ethanol) | 90 |
| Ib | 1-ethyl-3-carboxy-4-oxo-pyrazolo[5,4-h] quinoline | $C_{13}H_{11}O_3N_3$ | 270 | 20 |
| Ic | 1-ethyl-3-carboxy-4-oxo-pyrazolo[4,5-f]quinoline | $C_{13}H_{11}O_3N_3$ | 360 ACOH | 40 |
| Id | 1-ethyl-3-carboxy-4-oxo-7-benzyl-pyrazolo[4,5-f]quinoline | $C_{20}H_{17}O_3N_3$ | 240–250 (DMF) | 30 |
| Ie | 1-ethyl-3-carboxy-4-oxo-pyrazolo[5,4-f]quinoline | $C_{13}H_{11}O_3N_3$ | 314–315 (DMF) | 85 |
| Ie' | 1-vinyl-3-carboxy-4-oxo-pyrazolo[5,4-f]quinoline | $C_{13}H_9O_3N_3$ | 270 (DMF) | 20 |

TABLE V-continued

| N° | Name | Empirical Formula | M.p. (°C.) and crystallization solvent | Yield % |
|---|---|---|---|---|
| If | 1-ethyl-3-carboxy-4-oxo-5-methyl-pyrazolo[5,4-f]quinoline | $C_{14}H_{13}O_3N_3$ | 246-8 (DMF) | 73 |
| Ig | 1-ethyl-3-carboxy-4-oxo-6-methyl-pyrazolo[3,4-f]quinoline | $C_{14}H_{13}O_3N_3$ | 320 (DMF) | 40 |
| Ih | 1,9-diethyl-3-carboxy-4-oxo-pyrazolo[4,5-h]quinoline | $C_{15}H_{15}O_3N_3$ | 240-41 (ethanol) | 30 |

DMF = dimethylformamide
AcOH = acetic acid
DMSO = dimethylsulfoxide.

The compounds of the formula (I) possess outstanding antibacterial activities (particularly against Gram-negative bacteria) and are therapeutically useful as antibacterial agents.

The antimicrobial activity of the compounds of the formula (I) was demonstrated in vitro, by the dilution in liquid medium method, using nalidixic acid as reference material.

A—Preparation of antimicrobial solutions

The nalidixic acid solution and the solutions containing compounds of the formula (I) were prepared in distilled water with addition of sodium hydroxide.

B—Preparation of the bacterial inoculum

The strains used are all obtained from the hospital where they were recently isolated from urinary infections (except Salmonella para B and Listeria which are obtained from a collection):

Pseudomonas aeruginosa
Klebsiella pneumoniae
Proteus mirabilis
Escherichia coli
Citrobacter
Enterobacter cloacae
Enterobacter liquefaciens
Listeria monocytogenes
Salmonella para B
Streptococcus foecalis
Staphylococcus aureus Different dilutions of 24 hour cultures in physiological saline were used, depending on the respective growth rate of each germ:

| | |
|---|---|
| Listeria, Streptococcus | $10^{-1}$ |
| Citrobacter, Enterobacter | $10^{-2}$ |
| Other germs | $10^{-3}$ |

The test is conducted in phenol red glucose broth inoculated with 0.1 ml of the dilution of the germ studied per 3 ml of broth.

C—Test

The bactericidal activity was investigated according to the dilution in liquid medium method.

| Phenol red broth inoculated (ml) | 1.6 | 1.8 | 1.7 | 1.8 | 1.9 | 1.8 | 1.9 | 1.8 |
|---|---|---|---|---|---|---|---|---|
| Mother solution 1 mg/ml | 0.4 | 0.2 | | | | | | |
| Dilution 1/2 | | | 0.3 | 0.2 | 0.1 | | | |
| 1/10 | | | | | | 0.2 | 0.1 | |
| 1/100 | | | | | | | | 0.2 |
| Concentration (μg/ml) | 200 | 100 | 75 | 50 | 25 | 10 | 5 | 1 |

After 18 hours in an oven at 37° C., the minimum inhibiting concentration (MIC) corresponding to the last tube whose pH remains unmodified was noted.

The minimum bactericidal concentration (MBC) was investigated by spreading on a dish of agar medium a dosage of material taken from the tubes which have remained clear. The MBC/24 hrs is the lowest concentration for which the survival rate is zero after a contact time of 24 hours.

D—Results

The MIC results are given in μg/ml
Some MBC values are also given in μg/ml $R_{200}$ = germs resistant to concentrations of 200 μg/ml
$R_{10}$ = germs resistant to concentrations of 10 μg/ml
The results obtained are tabulated in the following Table.

in which:
R is selected from $C_{1-6}$ alkyl and $C_{1-6}$ alkenyl,
A is selected from indazol-4,5-diyl, indazol-6,7-diyl, and the same groups substituted on the nitrogen

| Compound n° | Pseudom. aerug. | Kelbs. penum. | Proteus mirab. | Escher. coli | Citrob. | Enterob. cloacae | Enterob. liquef. | Listeria monocty. | Salmon. para B | Strepto foec. | Staphyl. aureus |
|---|---|---|---|---|---|---|---|---|---|---|---|
| I a | >100 | >100 | >100 | >100 | — | — | — | — | >100 | >100 | >100 |
| I b | >100 | >100 | >100 | >100 | — | — | — | — | >100 | >100 | >100 |
| I c | >10 | >10 | >10 | >10 | — | — | — | — | — | >10 | >10 |
| I d | >10 | — | >10 | — | — | — | — | — | — | >10 | >10 |
| I e | $R_{10}$ | $R_{10}$ | $R_{10}$ | 5 MBC 100 | $R_{10}$ | $R_{10}$ | $R_{10}$ | 10 MBC 100 | $R_{10}$ | $R_{10}$ | $R_{10}$ |
| I e' | $R_{10}$ | $R_{10}$ | $R_{10}$ | 5 | $R_{10}$ | — | — | — | — | $R_{10}$ | $R_{10}$ |
| I f | >10 | — | >10 | — | — | — | — | — | — | >10 | >10 |
| I g | >100 | >100 | >100 | — | — | — | — | — | — | >100 | >100 |
| I h | >10 | >10 | >10 | — | — | — | — | — | — | >10 | >10 |
| Nalidixic acid | $R_{200}$ | $R_{200}$ | $R_{200}$ | 5 MBC 100 | $R_{200}$ | 50 MBC 100 | 25 MBC 100 | 5 MBC 100 | 5 MBC 100 | $R_{200}$ | $R_{200}$ |

It is apparent from said results that compounds (Ie) and (Ie′) are particularly active: about 20 times more active than nalidixic acid against Pseudomonas, Klebsiella, Proteus, Citrobacter, Streptococcus and Staphylococcus, from 2 to 5 times more active against Enterobacter, while they are substantially as active against Escherichia, Listeria and Salmonella.

Acute toxicity

Both compounds (Ie) and (Ie′) have a particularly low toxicity. Indeed, their $LD_{50}$ values in mice, as determined by the graphical method according to Miller and Tainter are as follows:

| Oral route | | Intraperitoneal route |
|---|---|---|
| Ie | 4.7 g/kg | 2.50 g/kg |
| Ie′ | >5.0 g/kg | 2.8 g/kg |

Thus, this invention relates also to therapeutic compositions comprising, as active ingredient, a compound of the formula (I) or a salt thereof with pharmaceutically acceptable bases, typically together with a pharmaceutically acceptable excipient.

The therapeutic compositions of this invention are administrable to humans, particularly by the oral, parenteral or local route.

The oral compositions comprise capsules or tablets containing 20–200 mg active ingredient.

The parenteral compositions comprise aqueous solutions containing 1–5% active ingredient in salt form, typically as salts with alkaline-earth metals or with organic bases.

The compositions for local administration comprise, inter alia, ointments, collyria, collutories, and the like, which contain 0.5–5% active ingredient.

Having now described our invention what we claim as new and desire to secure by Letters Patent is:

1. A compound selected from the group consisting of compounds of the formula

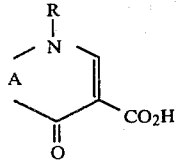

(I)

in which:
R is selected from $C_{1-6}$ alkyl and $C_{1-6}$ alkenyl,
A is selected from indazol-4,5-diyl, indazol-6,7-diyl, and the same groups substituted on the nitrogen atoms at 1- or 2-position with a substituent selected from $C_{1-6}$ alkyl and phenyl-($C_{1-6}$)alkyl
and a salt thereof with a pharmaceutically acceptable base.

2. A compound as claimed in claim 1, wherein R is selected from ethyl and vinyl and A is selected from unsubstituted indazoldiyl groups and the same substituted on the nitrogen atoms at 1- or 2-position with a substituent selected from methyl, ethyl or benzyl.

3. A compound as claimed in claim 1, which is selected from 1-ethyl-3-carboxy-4-oxo-pyrazolo[5,4-f]quinoline, 1-vinyl 3-carboxy-4-oxo-pyrazolo[5,4-f]quinoline, and their salts with pharmaceutically acceptable bases.

4. 1-vinyl-3-carboxy-4-oxo-pyrazolo[5,4-f]quinoline and its salts with pharmaceutically acceptable bases.

5. Therapeutic composition having an antibacterial activity, comprising an antibacterial effective amount of a compound selected from the group consisting of compounds of the formula

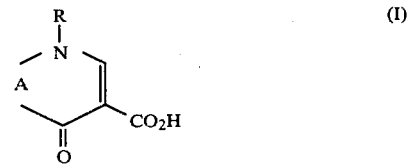

(I)

in which:
R is selected from $C_{1-6}$ alkyl and $C_{1-6}$ alkenyl,
A is selected from indazol-4,5-diyl, indazol-6,7-diyl, and the same groups substituted on the nitrogen atoms at 1- or 2-position with a substituent selected from $C_{1-6}$ alkyl and phenyl-($C_{1-6}$)alkyl,
and a salt thereof with a pharmaceutically acceptable base.

6. A therapeutic composition as claimed in claim 5, formulated in a form suitable for oral, parenteral or local administration.

* * * * *